United States Patent [19]

Bailey et al.

[11] Patent Number: 4,962,120

[45] Date of Patent: Oct. 9, 1990

[54] 1H-IMIDAZOLE-1-ACETAMIDES

[75] Inventors: Denis M. Bailey, East Greenbush; Virendra Kumar, Colonie, both of N.Y.

[73] Assignee: Sterling Drug Inc., New York, N.Y.

[21] Appl. No.: 327,227

[22] Filed: Mar. 22, 1989

[51] Int. Cl.$^5$ .............. C07D 233/61; C07D 401/12; C07D 403/12; A61K 31/415

[52] U.S. Cl. ............................ 514/399; 514/212; 514/326; 514/397; 514/400; 540/603; 546/210; 548/336; 548/341; 548/342

[58] Field of Search ............ 540/603; 514/212, 326, 514/397, 399, 400; 546/210; 548/336, 341, 342

[56] References Cited

U.S. PATENT DOCUMENTS 4,330,544  5/1982  Jarreau et al. .............. 548/374 X
4,410,525 10/1983  Jarreau et al. .............. 548/374 X

FOREIGN PATENT DOCUMENTS 299407  1/1989  European Pat. Off. .

OTHER PUBLICATIONS

Ezrin et al., *FASEB Journal* 2, A1557 (1988).
Iradyan et al., *Chemical Abstracts* 88:152498y (1978).
Iradvan et al., *Chemical Abstracts* 83:79153x (1975).
Abstract of EP 299,407, 1/18/89.

*Primary Examiner*—John M. Ford
*Attorney, Agent, or Firm*—Philip E. Hansen; Paul E. Dupont

[57] ABSTRACT

N-[(alkylamino)alkyl]-4,5-diaryl-1H-imidazole-1-acetamides useful for treating cardiac arrhythmias in mammals, are prepared by reacting a lower-alkyl ester of a diaryl imidazole-1-acetic acid with an appropriate diamine.

13 Claims, No Drawings

1H-IMIDAZOLE-1-ACETAMIDES

BACKGROUND OF THE INVENTION

1. Field of the Invention

The present invention relates to novel N-[(alkylamino)alkyl]-4,5-diaryl-1H-imidazole-1-acetamides, processes for the synthesis of said imidazole-1-acetamides, and methods for treating cardiac arrhythmia in mammals utilizing said imidazole-1-acetamides.

2. Information Disclosure Statement

Iradyan et al. [*Chemical Abstracts* 88: 152498y (1978)] disclose ethyl 4-(substituted-phenyl)-1H-imidazole-1-acetates wherein the substituted phenyl is 4-fluorophenyl, 4-chlorophenyl, 4-bromophenyl, 4-methoxyphenyl, 4-nitrophenyl, 4-ethoxyphenyl, or 4-propoxyphenyl.

Iradyan et al. [*CA* 83: 79153x (1975)] disclose the reaction of a potassium salt of a 4-arylimidazole with α-chloroacetamide to produce 4-phenyl-and 4-(substituted-phenyl)-1H-imidazole-1-acetamides wherein the substituted phenyl is 4-methoxyphenyl, 4-ethoxyphenyl, 4-propoxyphenyl, or 4-butoxyphenyl. No utility is disclosed in the abstract.

Ezrin et al. [*FASEB Journal* 2, A1557 (1988)] disclose N-[(diethylamino)propyl]-4,5-diphenyl-1H-pyrazole-1-acetamide fumarate as an antiarrhythmic agent.

European patent application No. 299407, published Jan. 18, 1989, discloses a series of 4,5-diaryl-1H-pyrazole-1-alkanamides as antiarrhythmic agents.

SUMMARY OF THE INVENTION

In a product aspect the invention relates to compounds of the formula I

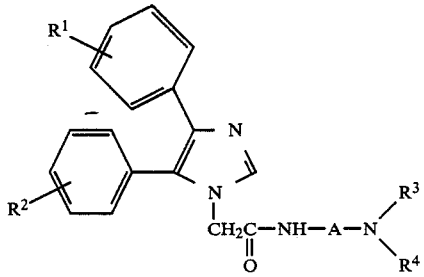

I or acid-addition salt or solvate thereof wherein $R^1$ and $R^2$ are independently hydrogen, hydroxy, lower-alkyl, lower-alkoxy, nitro, or halo; $R^3$ and $R^4$ are independently hydrogen, lower-alkyl, or hydroxy lower-alkyl, or $R^3$ and $R^4$ together form a straight or branched alkylene chain of four to six carbons; and A is $CH_2CH(OH)CH_2$ or $(CH_2)_n$ where n is an integer from two to eight.

Lower-alkyl as used herein describes linear or branched hydrocarbon chains of four or fewer carbon atoms; lower-alkoxy as used herein describes linear or branched alkyloxy substituents containing four or fewer carbon atoms; halogen describes bromine, chlorine or fluorine.

In a further product aspect, the invention relates to compositions for treating cardiac arrhythmia which comprise compounds of the formula I together with pharmaceutically acceptable excipients or diluents as required.

In a process aspect, the invention relates to a method for treating cardiac arrhthmia in a mammal which comprises administering to said mammal an antiarrhythmically effective amount of a compound of formula I.

Processes for preparing a compound of formula I comprise reacting an imidazole-1-acetate with an amine.

DETAILED DESCRIPTION INCLUSIVE OF PREFERRED EMBODIMENTS

The synthesis of compounds of the invention may be outlined as shown in scheme A wherein $R^5$ is lower-alkyl.

Scheme A

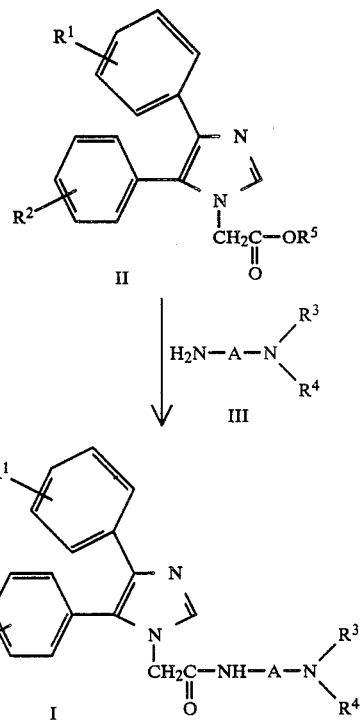

The lower-alkyl ester, preferably a methyl or ethyl ester, of the suitably substituted 4,5-diphenylimidazole-1-alkanoic acid (II) is reacted with an excess of a primary or secondary amine of formula III at 20° to 150° C., preferably at 90° to 150° C. When the amine is valuable, the ester II is preferably reacted with about one equivalent of the amine III in the presence of a tertiary amine, preferably diisopropylethylamine, optionally in an inert solvent.

The ester II may be synthesized from the appropriate 4,5-diarylimidazole by alkylation of an alkaline metal salt of the imidazole, preferably the sodium salt, with an α-haloacetic ester, preferably ethyl bromoacetate, in an inert solvent, preferably DMF, at 0° to 100° C. In the case where $R^1$ does not equal $R^2$, two isomers will be obtained which may be readily separated by crystallization or chromatography, or the mixture of isomers may be carried through the next step and separated as the amides. The diaryl imidazoles are commercially available, known in the art, or may be synthesized by methods well-known in the art.

The compounds of formula I are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the benefical properties inherent in the free base are not vitiated by side effects ascribable to the anions. In practicing the present invention it may be found convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, and nuclear magnetic resonance, spectroscopy. The course of the reactions and the identity and homogeneity of the products were assessed by thin layer chromatography (TLC). The starting materials are either commercially available or may be prepared by procedures well known in the art.

In the following procedures melting points are given in degrees C and are uncorrected. The abbreviation THF stands for tetrahydrofuran, DMF stands for N,N-dimethylformamide and Ac stands for the acetyl residue, CH3CO.

EXAMPLE 1

Ethyl 4,5-diphenyl-1H-imidazole-1-acetate

To a stirred suspension of 9.6 (0.24 mol) of 60% sodium hydride-mineral oil in 100 mL of DMF under nitrogen at 0° C. was added dropwise 50.0 g (0.226 mol) of 4,5-diphenylimidazole in 400 mL DMF. The mixture was allowed to warm, stirred at room temperature 1 hr, and 26.6 mL (0.24 mol) of ethyl bromoacetate was added. The reaction was stirred 18 hr at room temperature, heated on a steam bath 2 hr, cooled, and stripped. The residue was partitioned between water and methylene chloride, dried over MgSO4, and filtered through a silica gel column eluting with methylene chloride-ethyl acetate to provide 50.1 g of an oil that solidified on standing. It may be used in further reactions as is, or it may be recrystallized from ether to yield 35.1 g of product mp 89°–90° C.

EXAMPLE 2

Ethyl 4,5-bis(2-methoxyphenyl)-1H-imidazole-1-acetate

By a process substantially similar to that of example 1, it is contemplated that ethyl 4,5-bis(2-methoxyphenyl)-1H-imidazole-1-acetate may be synthesized from 4,5-bis(2-methoxyphenyl)-1H-imidazole and ethyl bromoacetate.

EXAMPLE 3

Ethyl 4-(4-chlorophenyl)-5-phenyl-1H-imidazole-1-acetate

By a process substantially similar to that of example 1, it is contemplated that ethyl 4-(4-chlorophenyl)-5-phenyl-1H-imidazole-1-acetate may be synthesized from 4-(4-chlorophenyl)-5-phenyl-1H-imidazole and ethyl bromoacetate.

EXAMPLE 4

N-[3-(Diethylamino)propyl]-4,5-diphenyl-1H-imidazole-1-acetamide

A solution of 36.0 g (0.117 mol) of ethyl 4,5-diphenyl-1H-imidazole of example 1 in 80 mL of 3-(diethylamino)propanamine was heated at 100° for 6 hrs, cooled, the excess amine was removed in vacuo, and the residue was recrystallized twice from ether to yield 8.0 g of product, mp 81°–83° C.

EXAMPLE 5

N-[3-(Dimethylamino)propyl]-4,5-diphenyl-1H-imidazole-1-acetamide

A suspension of 5.0 g (10.3 mmol) of ethyl 4,5-diphenyl-1H-imidazole of example 1 in 3.1 mL (24.5 mmol) of 3-(dimethylamino)propanamine was heated at 100° C. for 6 hr. The reaction was poured into ice-water and held at 0° overnight. The resulting solid was filtered off, dried and recrystallized from ether-hexane to yield 4.6 g of product, mp 92°–94° C.

EXAMPLE 6

N-[3-[(1,1-Dimethylethyl)amino]propyl]-4,5-diphenyl-1H-imidazole-1-acetamide

A mixture of 7.0 g (23 mmol) of ethyl 4,5-diphenyl-1H-imidazole-1-acetate of example 1 and 4.5 g (34.6 mmol) of 3-(t-butylamino)propylamine, conveniently made by LAH reduction of 3-(t-butylamino)propionitrile in THF, was heated at 100° C. for 8 hr. The residue was distributed between water and methylene chloride, and the methylene chloride layer was dried over MgSO4 and stripped. The residue was recrystallized from ether and then cyclohexane to yield 4.5 g of product, mp 94°–96° C.

EXAMPLE 7

N-[3-(Diethylamino)-2-hydroxypropyl]-4,5-bis(2-methoxyphenyl)-1H-imidazole-1-acetamide By a procedure substantially similar to that of example 6, it is contemplated that N-[3-(Diethylamino)-2-hydroxypropyl]4,5-bis(2-methoxyphenyl)-1H-imidazole-1-acetamide may be synthesized from ethyl 4,5-bis(2-methoxyphenyl)-1H-imidazole-1-acetate of example 2 and 1-amino-3-diethylamino-2-propanol.

EXAMPLE 8

4-(4-Chlorophenyl)-5-phenyl-N-[3-(1-pyrrolidinyl)ethyl]-1H-imidazole-1-acetamide By a procedure substantially similar to that of example 6, it is contemplated that 4-(4-chlorophenyl)-5-phenyl-N-[3-(1-pyrrolidinyl)ethyl]-1H-imidazole-1-acetamide may be synthesized from ethyl 4-(4-chlorophenyl)-5-phenyl-1H-imidazole-1-acetate of example 3 and N-(2-aminoethyl)pyrrolidine.

The antiarrhythmic activity of compounds of the invention was demonstrated by the following procedure.

Duncan Hartley guinea pigs (600–900 grams) of either sex were anesthetized with urethane (1.4 g/kg, i.p.) and supplemented as needed. An intravenous route for drug administration was established using microbore tubing inserted into the jugular vein. The induction of arrhythmias by aconitine hydrochloride (34 g/kg) was evaluated in control guinea pigs given 1 cc saline as an intravenous bolus 10 minutes prior to aconitine challenge.

Compounds to be tested were administered intravenously 10 minutes prior to aconitine challenge at an initial dosage of 30 mg/kg. This dosage was reduced in subsequent animals if severe cardiac rhythm disturbances persisted beyond two minutes after injection in the first guinea pig tested. All drugs were tested at the maximally tolerated dose (identified by the lack of arrhythmias in the EKG prior to aconitine challenge). Compounds were administered in saline as 1 cc bolus injections (n=4–6).

Time intervals between aconitine injection and the appearance of arrhythmias were determined. Specifically noted was the time until the onset of (i) the first premature ventricular contraction (PVC); (ii) the first sustained run of ventricular tachycardia consisting of 10 or more ventricular beats (VTACH); and (iii) the time until the appearance of ventricular fibrillation lasting longer than 15 seconds (VFIB). The average time and standard error of the mean until the appearance of these arrhythmias were calculated for each treatment group and compared to concurrent controls using a one-way analysis of variance. Activity was defined as a statistically significant delay in the onset of PVC, VTACH and VFIB time course compared to control values.

The following table summarizes the results obtained from the testing of representative compounds of the invention.

| Example No. | Minutes to | | |
|---|---|---|---|
| | PVC | VTACH | VFIB |
| Control | 1.0–2.1 | 1.3–2.5 | 3.1–6.3 |
| 4 | 8.1 | 34.0 | 60.0 |
| 5 | 12.3 | 30.6 | 60.0 |
| 6 | 13.5 | 20.9 | 45.2 |

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

I claim:

1. A compound of formula

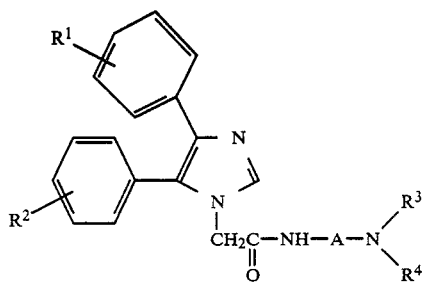

or acid-addition salt thereof wherein $R^1$ and $R^2$ are independently hydrogen, hydroxy, lower-alkyl, lower-alkoxy, nitro, or halo; $R^3$ and $R^4$ are independently hydrogen, lower-alkyl, or hydroxy lower-alkyl, or $R^3$ and $R^4$ together form a straight or branched alkylene chain of four to six carbons; A is $CH_2CH(OH)CH_2$ or $(CH_2)_n$ wherein n is an integer from two to eight.

2. A compound according to claim 1 wherein A is $(CH_2)_n$ and n is two or three.

3. A compound according to claim 2 wherein $R^3$ and $R^4$ are both lower-alkyl.

4. N-[3-(Diethylamino)propyl]-4,5-diphenyl-1H-imidazole-1-acetamide according to claim 3.

5. N-[3-(Dimethylamino)propyl]-4,5-diphenyl-1H-imidazole-1-acetamide according to claim 3.

6. A compound according to claim 2 wherein $R^3$ is hydrogen and $R^4$ is lower-alkyl.

7. N-[3-[(1,1-Dimethylethyl)amino]propyl]-4,5-diphenyl-1H-imidazole-1-acetamide according to claim 6.

8. A composition for treating cardiac arrhythmias comprising an amount of a compound according to claim 1 effective to treat cardiac arrhythmias together with one or more pharmaceutically acceptable excipients or diluents.

9. A composition for treating cardiac arrhythmias comprising an amount of a compound according to claim 3 effective to treat cardiac arrhythmias together with one or more pharmaceutically acceptable excipients or diluents.

10. A composition for treating cardiac arrhythmias comprising an amount of N-[3-(diethylamino)propyl]-4,5-diphenyl-1H-imidazole-1-acetamide or pharmaceutically acceptable acid addition salt or solvate thereof according to claim 4 effective to treat cardiac arrhythmias together with one or more pharmaceutically acceptable excipients or diluents.

11. A method for treating cardiac arrhythmias in a susceptible subject which comprises the step of administering an amount of a compound according to claim 1 effective to treat cardiac arrhythmias.

12. A method for treating cardiac arrhythmias in a susceptible subject which comprises the step of administering an amount of a compound according to claim 3 effective to treat cardiac arrhythmias.

13. A method for treating cardiac arrhythmias in a susceptible subject which comprises the step of administering an amount of N-[3-(diethylamino)propyl]-4,5-diphenyl-1H-imidazole-1-acetamide or pharmaceutically acceptable acid addition salt or solvate thereof according to claim 12 effective to treat cardiac arrhythmias.

* * * * *